(12) United States Patent
Parvin et al.

(10) Patent No.: US 9,031,306 B2
(45) Date of Patent: May 12, 2015

(54) DIAGNOSTIC AND PROGNOSTIC HISTOPATHOLOGY SYSTEM USING MORPHOMETRIC INDICES

(71) Applicant: The Regents of the University of California, Oakland, CA (US)

(72) Inventors: Bahram Parvin, Mill Valley, CA (US); Hang Chang, Moraga, CA (US); Ju Han, Albany, CA (US); Gerald V. Fontenay, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 120 days.

(21) Appl. No.: 13/886,213

(22) Filed: May 2, 2013

(65) Prior Publication Data
US 2013/0294676 A1 Nov. 7, 2013

Related U.S. Application Data

(60) Provisional application No. 61/641,798, filed on May 2, 2012.

(51) Int. Cl.
*G06K 9/00* (2006.01)
*G06T 7/00* (2006.01)
*A61B 5/00* (2006.01)

(52) U.S. Cl.
CPC ............ *A61B 5/0033* (2013.01); *A61B 5/7275* (2013.01); *G06T 7/0014* (2013.01); *G06T 2207/20076* (2013.01); *G06T 2207/30024* (2013.01); *G06T 2207/30096* (2013.01)

(58) Field of Classification Search
CPC .................................. A61B 5/00; G06T 7/00
USPC ........... 382/128–134; 600/407, 410, 411, 427
See application file for complete search history.

(56) References Cited

U.S. PATENT DOCUMENTS

| 8,488,863 B2 * | 7/2013 | Boucheron | 382/133 |
| 2010/0177950 A1 * | 7/2010 | Donovan et al. | 382/133 |

OTHER PUBLICATIONS

Han, J. et al. "Multivariate Characterization of Cell Surface Proteins," Life Science Division, Lawrence Berkeley National Laboratory, 31-36.
Han, J. et al. "Comparison of Sparse Coding and Kernel Methods for Histopathological Classification of Gliobastoma Multiforme," Life Science Division, Lawrence Berkeley National Laboratory, 37-40.
Loss, L.A. (Aug. 2011). "Iterative Tensor Voting for Perceptual Grouping of I11-Defined Curvilinear Structures," IEEE Transactions on Medical Imaging, 30(8):1503-1513.
Chang, H. et al. (2011). "Morphometic Analysis of TCGA Glioblastoma Multiforme," BMC Bioinformatics, 12 (484):1-12.
Le, Q.V. et al. "Learning Invariant Features of Tumor Signatures," Department of Computer Science, Stanford University, 64-67.
Chang, H. et al. (2011). "Batch-Invariant Nuclear Segmentation in Whole Mount Histology Sections," Life Science Division, Lawrence Berkeley National Laboratory, 68-71.
Han, J. et al. "Molecular Bases of Morphometric Composition in Glioblastoma Multiforme," Life Science Division, Lawrence Berkeley National Laboratory, 72-75.

* cited by examiner

*Primary Examiner* — Abolfazl Tabatabai
(74) *Attorney, Agent, or Firm* — Lowenstein Sandler LLP

(57) ABSTRACT

Determining at least one of a prognosis or a therapy for a patient based on a stained tissue section of the patient. An image of a stained tissue section of a patient is processed by a processing device. A set of features values for a set of cell-based features is extracted from the processed image, and the processed image is associated with a particular cluster of a plurality of clusters based on the set of feature values, where the plurality of clusters is defined with respect to a feature space corresponding to the set of features.

20 Claims, 9 Drawing Sheets

US 9,031,306 B2

DIAGNOSTIC AND PROGNOSTIC HISTOPATHOLOGY SYSTEM USING MORPHOMETRIC INDICES

RELATED APPLICATIONS

This application is a non-provisional application of and claims priority to U.S. Provisional Patent App. No. 61/641,798 filed May 2, 2012, which is hereby incorporated by reference in its entirety.

STATEMENT OF GOVERNMENT SUPPORT

This work was supported by Grant Nos. CA140663 and CA1437991 awarded by the National Institute of Health and by Contract DE-AC02-05CH11231 awarded by the Department of Energy. The government has certain rights in this invention.

FIELD

Embodiments of the present invention relate to data processing, and particularly relates to a system and method for determining one or both of a prognosis and a therapy for a patient based on a stained tissue section of the patient.

BACKGROUND

Selecting an appropriate therapy for a cancer patient may be facilitated when the patient's cancer can be classified as belonging to a particular type of cancer associated with a particular group of patients. For example, various properties of cancer cells identified from a stained tissue section of the patient may be characteristic of cancer cell properties exhibited by other patients in a particular group. When a patient's cancer can be classified in this manner, survival and therapy data for the other patients of this particular group can be used to formulate a prognosis and inform selection of an appropriate therapy.

DETAILED DESCRIPTION

Figure 1:
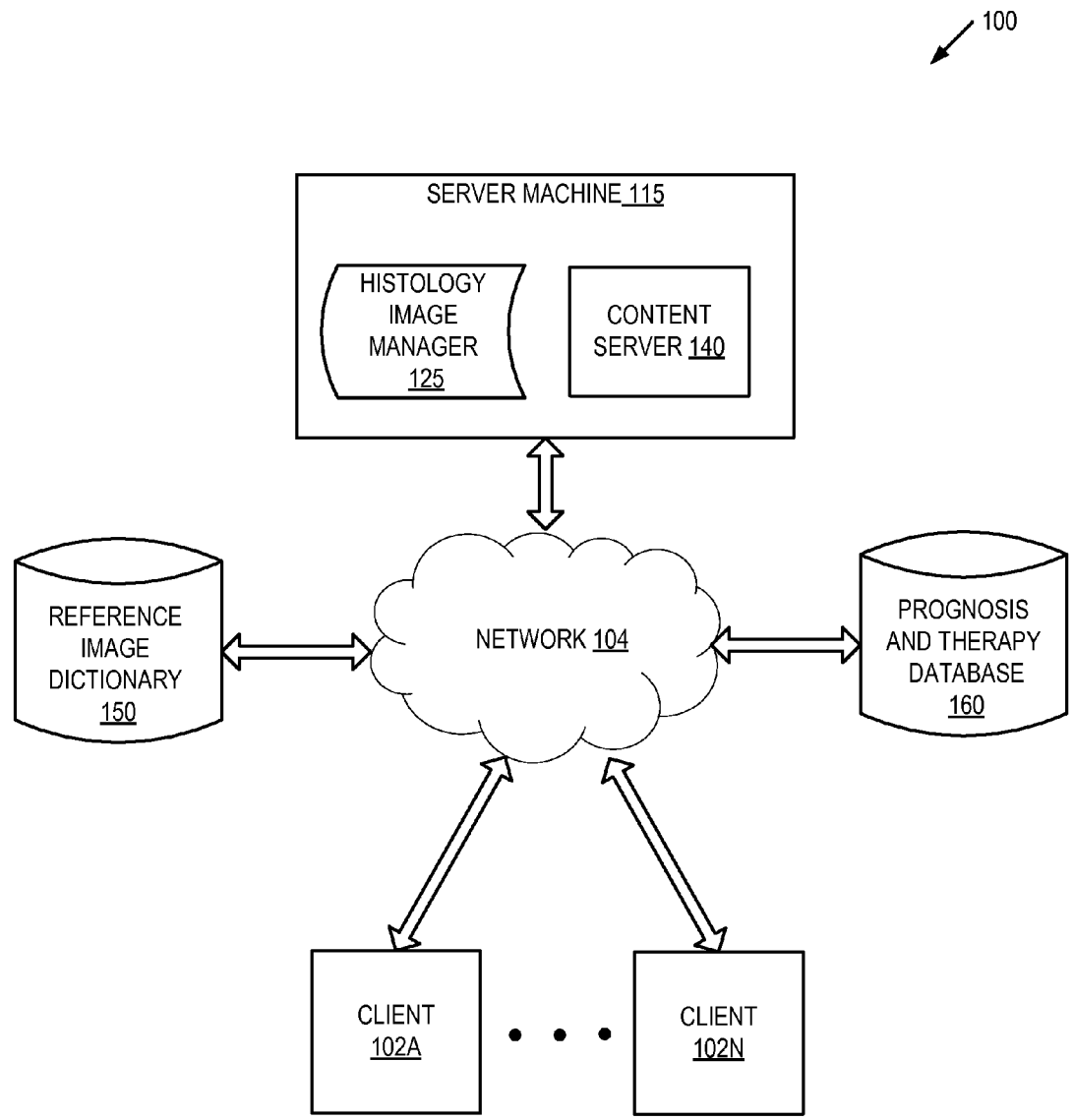
FIG. 1 illustrates a system architecture, in accordance with one implementation of the present disclosure.

A system and methods are disclosed for determining a prognosis and therapy for a patient based on a stained tissue sample or section obtained from a patient. Briefly, the tissue sample can be a biopsy from any tissue suspected of having disease, for example, cancer. In some embodiments, the tissue is a tissue such as an epithelial tissue, breast, skin, pancreatic, ovarian, colon, prostate, head and neck, etc. In various embodiments, the biopsy is of a tumor suspected to be invasive, metastatic, or tumorigenic. The sample is often submitted to sample preparation techniques such as paraffin blocking, staining with stains such as H&E and analyzed by a pathologist to determine if the biopsied tissue contains a tumor cells, the stage and grade the tumor and disease, if cancerous. Images of the stained tissue samples can be made using known microscopy imaging techniques and electronically stored images of the samples can be made or stored in, or uploaded to the described system.

Thus, in one embodiment, an image of a stained tissue section of a patient is received by a server (e.g., via upload over the Internet, etc.). A subimage is extracted from the image and processed by the server to obtain a set of feature values for the subimage (e.g., average nuclear size, maximum nuclear size, minimum nuclear size, variance in nuclear size, cellularity, etc.). The subimage is associated with a particular cluster in a feature space based on one or more of the feature values, which identifies a particular morphometric subtype. When the morphometric subtype is prognosis-predictive, a prognosis and therapy for the patient are determined using a database comprising historical data (e.g., patient survival data, etc.) and subtype-prognosis-therapy associations obtained from the historical data.

In some embodiments, a pathologist may make a section of a biopsy taken from a patient and images of the section and upload the images to the system. The system processes the image and determines a prognosis and diagnosis, and then provides the results to a clinician. A specific type of therapy is then prescribed to the patient based on the prognosis and diagnosis.

In one embodiment, the system supports two methods for subtyping based on computed morphometric indices. Subtyping can be performed as a function of (i) computed cellular profiles computed from the entire whole mount tissue sections across patients, or (ii) computed cellular profiles on a 1 k-by-1 k subimages across the entire cohort and independent of patient histology sections. In the first case, subtyping aims to identify stable clusters and to enable outcome-based (e.g., prognostic, predictive) analysis. In the second case, subtyping aims to identify patterns (e.g., a set of vocabularies) that enable each whole mount histology section to be represented. As a result of computed vocabularies, tumor composition can be computed, and heterogeneity characterized.

In one embodiment, the system delineates each cell, from whole slide images, and profiles each cell in terms of its morphometric properties (e.g., area, organization, cellularity) or protein expression. The system overcomes intrinsic barriers, through image-based modeling, associated with the batch effect that is associated in a large cohort; and biological heterogeneity that is associated between patients.

In one embodiment, the system captures tumor heterogeneity so that the outcome can be quantified in terms of heterogeneity. Therefore, one can test if heterogeneous tumor is more virulent. Through processing a large cohort of histology sections, collected from different patients, the system can compute subtypes and identify molecular basis (e.g., from genome-wide transcriptome or copy number) of each subtype to hypothesize aberrant biological processes for targeted therapy.

In one embodiment, a pipeline is built using univariate and multivartiate association techniques to link genome-wide molecular data with histopathological descriptors at multiple levels: (i) designing an interface for seamless integration with Regulome Explorer, (ii) identifying molecular basis of computed subtypes at patient level, (iii) probing for the molecular basis of computed heterogeneity indices, and (iv) validating whether phenotypic and/or genomic markers can improve predictability through interactions with clinical trials.

FIG. 1 illustrates a system architecture 100, in accordance with one embodiment of the present disclosure. The system architecture 100 includes a server machine 115, a reference image dictionary 150, a prognosis and therapy database 160, and client machines 102A-102N connected to a network 104. Network 104 may be a public network (e.g., the Internet), a private network (e.g., a local area network (LAN) or wide area network (WAN)), or a combination thereof.

The client machines 102A-102N may be personal computers (PCs), laptops, mobile phones, tablet computers, set top boxes, televisions, video game consoles, digital assistants or any other computing devices. The client machines 102A-102N may run an operating system (not shown) that manages hardware and software of the client machines 102A-102N. A browser (not shown) may execute on some client machines (e.g., on the OS of the client machines). The browser may be a web browser that can access content served by a content server 140 by navigating to web pages of the content server 140 (e.g., using the hypertext transport protocol (HTTP)). The browser may issue queries and commands to the content server 140, such as commands to upload images, download images, request processing of images, request classification of an image, request a prognosis based on an image, request a therapy based on an image, and so forth.

In general, functions described in one embodiment as being performed by the content server 140 can also be performed on the client machines 102A-102N in other embodiments if appropriate. In addition, the functionality attributed to a particular component can be performed by different or multiple components operating together. The content server 140 can also be accessed as a service provided to other systems or devices through appropriate application programming interfaces, and thus is not limited to use in websites.

Server machine 115 may be a rackmount server, a router computer, a personal computer, a portable digital assistant, a mobile phone, a laptop computer, a tablet computer, a camera, a video camera, a netbook, a desktop computer, a media center, or any combination of the above. Server machine 115 includes a content server 140 and a histology image manager 125. In alternative implementations, the content server 140 and histology image manager 125 may run on different machines.

Reference image dictionary 150 is a persistent storage that is capable of storing images of stained tissue sections. In one embodiment, reference image dictionary 150 stores a set of 1000 pixel by 1000 pixel images that are extracted from stained tissue sections and that are selected by a human expert as constituting a representative dictionary of diverse images. As described in detail below with respect to FIG. 8, images that are received for analysis are normalized against each of the images in this human-curated dictionary, thereby resulting in normalized images that are invariant to technical variation (e.g., different laboratories, different stains, different personnel, etc.). Reference image dictionary 150 may be hosted by one or more storage devices, such as main memory, magnetic or optical storage based disks, tapes or hard drives, NAS, SAN, and so forth. In some implementations, reference image dictionary 150 may be a network-attached file server, while in other embodiments reference image dictionary 150 may be some other type of persistent storage such as an object-oriented database, a relational database, and so forth, that may be hosted by the server machine 115 or one or more different machines coupled to the server machine 115 via the network 104. In some implementations, reference image dictionary 150 may be provided by a third-party service, while in some other implementations reference image dictionary 150 may be maintained by the same entity maintaining server machine 115.

Prognosis and therapy database 160 stores historical data pertaining to patients (e.g., survival data, therapy data, etc.), morphometric subtypes, and associations between prognostic-predictive morphometric subtypes, prognoses, and therapies. Prognosis and therapy database 160 may be hosted by one or more storage devices, such as main memory, magnetic or optical storage based disks, tapes or hard drives, NAS, SAN, and so forth. In some implementations, prognosis and therapy database 160 may be a relational database, an object-oriented database, etc. that is hosted by the server machine 115 or one or more different machines coupled to the server machine 115 via the network 104. In some implementations, prognosis and therapy database 160 may be provided by a third-party service, while in some other implementations prognosis and therapy database 160 may be maintained by the same entity maintaining server machine 115.

In accordance with some implementations, histology image manager 125 is capable of extracting subimages from histology images, normalizing images with respect to reference images in reference image dictionary 150, generating Gaussian Mixture Models for images, determining global and local fitness terms and applying the fitness terms to images, determining graph cuts of images, applying geometric reasoning to images, extracting features from images, determining morphometric subtypes based on features, storing associations of morphometric subtypes, prognoses and therapies in prognosis and therapy database 160, and determining prognoses and therapies for patients based on morphometric subtypes. An implementation of histology image manager 125 is described in detail below and with respect to FIG. 2.

Figure 2:
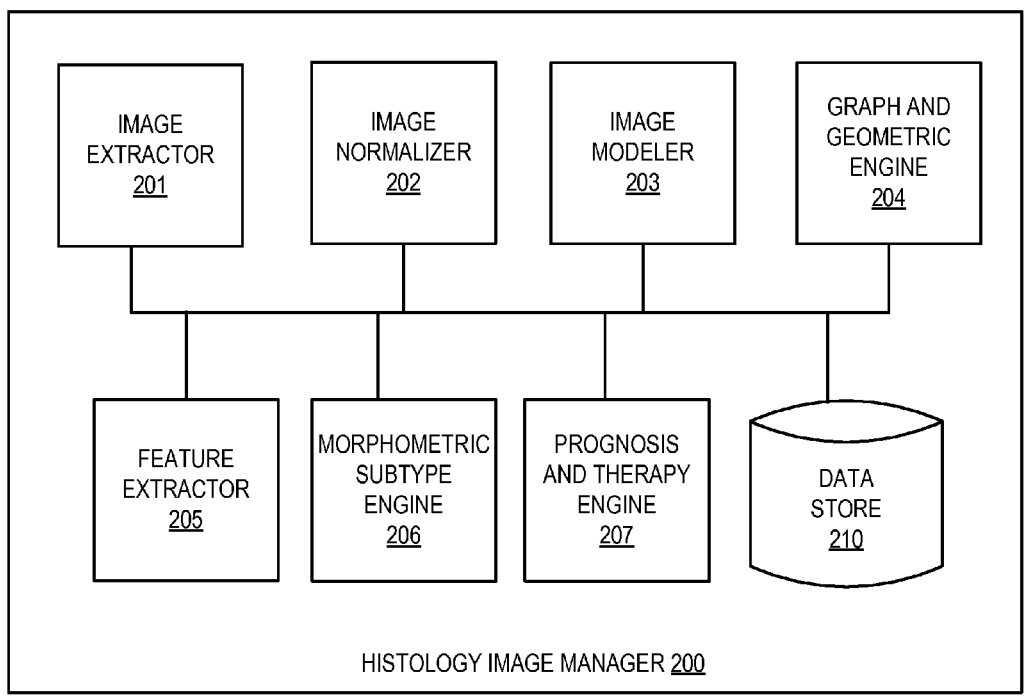
FIG. 2 is a block diagram of one embodiment of a histology image manager.

FIG. 2 is a block diagram of one implementation of a histology image manager. The histology image manager 200 may be the same as the histology image manager 125 of FIG. 2 and may include an image extractor 201, an image normalizer 202, an image modeler 203, a graph and geometric engine 204, a feature extractor 205, a morphometric subtype engine 206, a prognosis and therapy engine 207, and a data store 210. The components can be combined together or separated in further components, according to a particular implementation. It should be noted that in some implementations, various components of histology image manager 200 may run on separate machines.

The data store 210 may be the same as reference image dictionary 150, or prognosis and therapy database 160, or both, or may be a different data store (e.g., a temporary buffer or a permanent data store) to hold one or more images (e.g., to be stored in or retrieved from reference image dictionary 150, to be stored in or retrieved from prognosis and therapy database 160, to be processed, to be embedded in web pages, etc.), one or more data structures for indexing images in reference image dictionary 150 and prognosis and therapy database 160, one or more web pages to be served to clients, feature values associated with images, or some combination of these data. Data store 210 may be hosted by one or more storage devices, such as main memory, magnetic or optical storage based disks, tapes or hard drives, and so forth.

The image extractor 201 is capable of extracting one or more subimages (e.g., blocks of 1000-by-1000 pixels, etc.) from an image of a stained tissue section. (For convenience, the subimages will be referred to simply as images in the remainder of the detailed description.) The image normalizer 202 is capable of normalizing an image against each of the images in the reference image dictionary 150 in a color space (e.g., red-green-blue [RGB] space, Laplacian of Gaussian [LoG] space, etc.). In one embodiment, the image representation comprises obtaining an LoG-space representation of the image from a "blue ratio" representation, where the blue ratio of a pixel (x, y) is computed by the equation:

$$BR(x, y) = \frac{100 \cdot B(x, y)}{1 + R(x, y) + G(x, y)} \cdot \frac{256}{1 + B(x, y) + R(x, y) + G(x, y)}$$

where BR(x, y) is the blue ratio for a pixel (x, y), and R(x, y), G(x, y) and B(x, y) are the red, green and blue intensities, respectively, for pixel (x, y). One particular technique for normalizing images in this manner is described in detail in S. Kothari, J. H. Phan, R. A. Moffitt, T. H. Stokes, S. E. Hassberger, Q. Chaudry, A. N. Young, and M. D. Wang, "*Automatic batch-invariant color segmentation of histological cancer images*," in *Proc. Int. Symp. Biomed. Imag.*, 2011, pp. 657-660, which is incorporated by reference in its entirety.

The image modeler 203 is capable of generating a mathematical model of an image (e.g., of an image normalized by image normalizer 202, etc.). In one embodiment, image modeler 203 uses global and local fitness terms to generate a Gaussian Mixture Model of the image. One particular technique for generating Gaussian Mixture Models for images is referenced below with respect to FIG. 8 and is described in detail in *IEEE Trans Med Imaging.* 2013 *April;* 32(4):670-82. *doi:* 10.1109/TMI.2012.2231420. *Epub* 2012 *Dec.* 4. *Invariant delineation of nuclear architecture in glioblastoma multiforme for clinical and molecular association*. Chang H, Han J, Borowsky A, Loss L, Gray J W, Spellman P T, Parvin B., which is incorporated by reference in its entirety.

The graph and geometric engine 204 is capable of detecting points of maximum curvature along contours of a nuclear mask obtained from an image, of obtaining a triangulation of the points of maximum curvature by computing a Delaunay triangulation, of identifying line segments connecting nuclei in an image by applying geometric constraints and pruning to line segments of the triangulation, of representing an image as a graph with nodes of the graph corresponding to nuclei in the image and edges of the graph corresponding to the identified line segments, and of determining a graph cut of the graph representation of the image. Particular techniques for performing these operations are described in detail in Quan Wen, Hang Chang, Bahram Parvin: *A Delaunay Triangulation Approach for Segmenting Clumps of Nuclei. ISBI* 2009: 9-12, which is incorporated by reference in its entirety.

The feature extractor 205 is capable of extracting values of features (e.g., average nuclear size, maximum nuclear size, minimum nuclear size, variance in nuclear size, cellularity, etc.) from images via image processing techniques. One particular technique for extracting feature values is described in detail in Ju Han, Hang Chang, Kumari L. Andarawewa, Paul Yaswen, Mary Helen Barcellos-Hoff, Bahram Parvin: *Multidimensional Profiling of Cell Surface Proteins and Nuclear Markers. IEEE/ACM Trans. Comput. Biology Bioinform.* 7(1): 80-90 (2010), which is incorporated by reference in its entirety.

The morphometric subtype engine 206 is capable of performing clustering of feature values in a feature space over a plurality of images to obtain morphometric subtypes, and of determining a morphometric subtype for a particular image based on feature values of the image obtained by feature extractor 205. Particular techniques for clustering and determining morphometric subtypes are referenced below with respect to FIGS. 6 and 7 and are described in detail in Ju Han, Hang Chang, Kumari L. Andarawewa, Paul Yaswen, Mary Helen Barcellos-Hoff, Bahram Parvin: *Multidimensional Profiling of Cell Surface Proteins and Nuclear Markers. IEEE/ACM Trans. Comput. Biology Bioinform.* 7(1): 80-90 (2010), which is incorporated by reference in its entirety.

The prognosis and therapy engine 207 is capable of populating prognosis and therapy database 260 with records that associate morphometric subtypes, prognoses, and therapies, and of submitting queries to prognosis and therapy database 260 to determine a prognosis and therapy for a particular morphometric subtype. Some operations of prognosis and therapy engine 207 are described below with respect to FIGS. 3 through 6.

Figure 3:
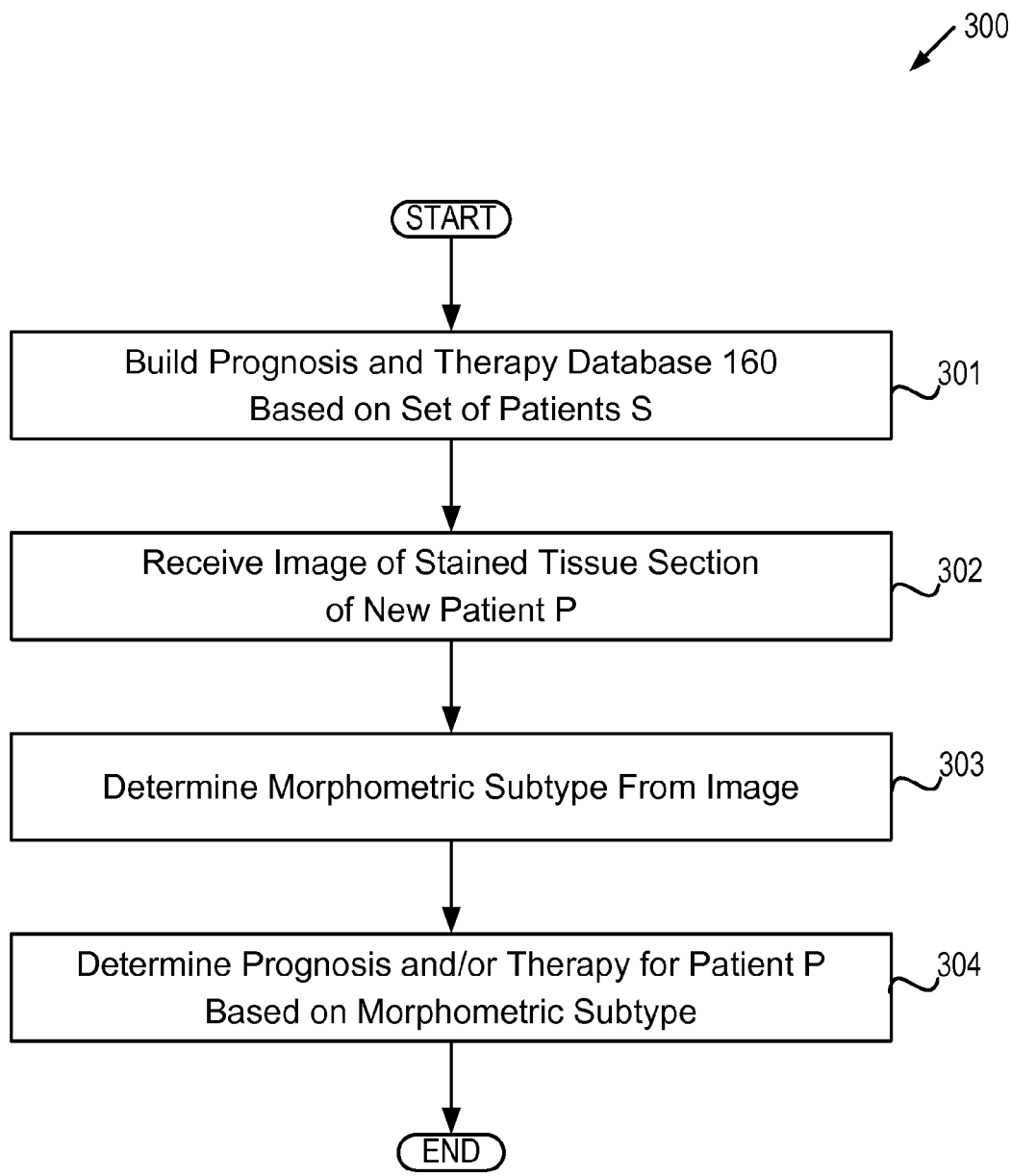
FIG. 3 depicts a flow diagram of an embodiment of a method for building and using a prognosis and therapy database.

FIG. 3 depicts a flow diagram of an embodiment of a method 300 for building and using a prognosis and therapy database. The method is performed by processing logic that may comprise hardware (circuitry, dedicated logic, etc.), software (such as is run on a general purpose computer system or a dedicated machine), or a combination of both. In one embodiment, the method may be performed by server machine 115 of FIG. 1, and more particularly, by histology image manager 125, while in some other embodiments, one or more blocks of FIG. 3 may be performed by some other machine.

For simplicity of explanation, methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term article of manufacture, as used herein, is intended to encompass a computer program accessible from any computer-readable device or storage media.

At block 301, prognosis and therapy database 160 is built based on a set S of patients. An implementation of a method for performing block 301 is described in detail below with respect to FIG. 4.

At block 302, an image of a stained tissue section of a new patient P (e.g., a patient that is not in the set S used to build prognosis and therapy database 160) is received. In one implementation, the image may be uploaded by a client 102 and received by content server 140 of server machine 115.

At block 303, a morphometric subtype is determined based on the image received at block 302. An implementation of a method for performing block 303 is described in detail below with respect to FIG. 7.

At block 304, one or both of a prognosis and a therapy are determined for patent P based on the morphometric subtype determined at block 303. In one implementation, a query is submitted to prognosis and therapy database 160 that ascertains whether the morphometric subtype is prognostic-predictive and, if so, retrieves one or both of a prognosis and a therapy based on the morphometric subtype. In one such implementation, prognosis and therapy engine 207 submits a query to prognosis and therapy database 160 to retrieve a prognosis and/or a therapy from an appropriate entry of a table that associates prognostic-predictive morphometric subtypes with prognoses and therapies. If no such entry is found for the morphometric subtype, then it is concluded that the morphometric subtype is not prognostic-predictive (and in accordance with this implementation, the morphometric subtype belongs to an entry of another table in prognosis and therapy database 160 that stores non-predictive subtypes).

Figure 4:
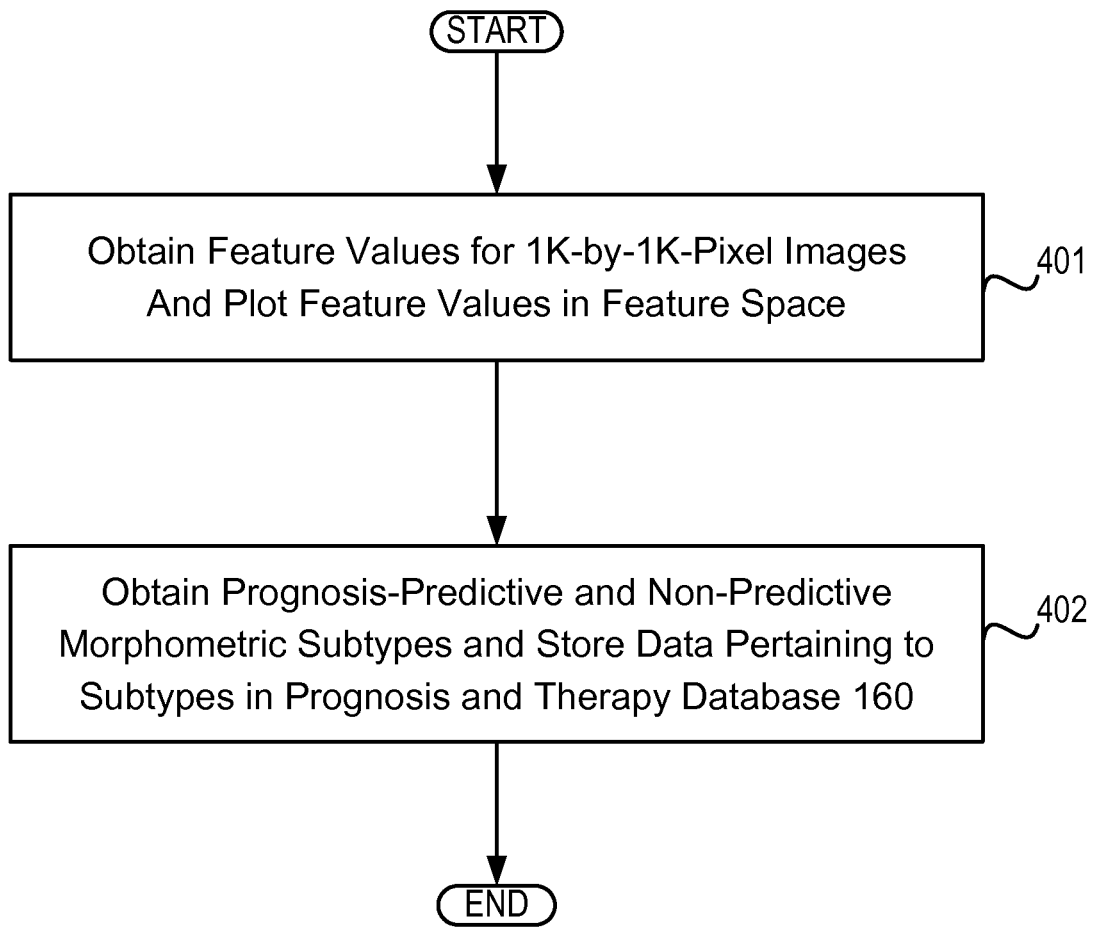
FIG. 4 depicts a flow diagram of an embodiment of a method for building a prognosis and therapy database.

FIG. 4 depicts a flow diagram of an embodiment of a method for building a prognosis and therapy database. The method is performed by processing logic that may comprise hardware (circuitry, dedicated logic, etc.), software (such as is run on a general purpose computer system or a dedicated machine), or a combination of both. In one embodiment, the method may be performed by server machine 115 of FIG. 1, and more particularly, by histology image manager 125, while in some other embodiments, one or more blocks of FIG. 4 may be performed by some other machine.

At block 401, cell-based feature values are repeatedly obtained for each 1K-by-1K-pixel images extracted from the whole slide stained tissue sections for each patient of the set S. An implementation of a method for performing block 401 is described in detail below with respect to FIG. 5.

At block 402, prognosis-predictive morphometric subtypes and non-predictive morphometric subtypes are obtained and data pertaining to the morphometric subtypes is stored in prognosis and therapy database. An implementation of a method for performing block 402 is described in detail below with respect to FIG. 6.

Figure 5:
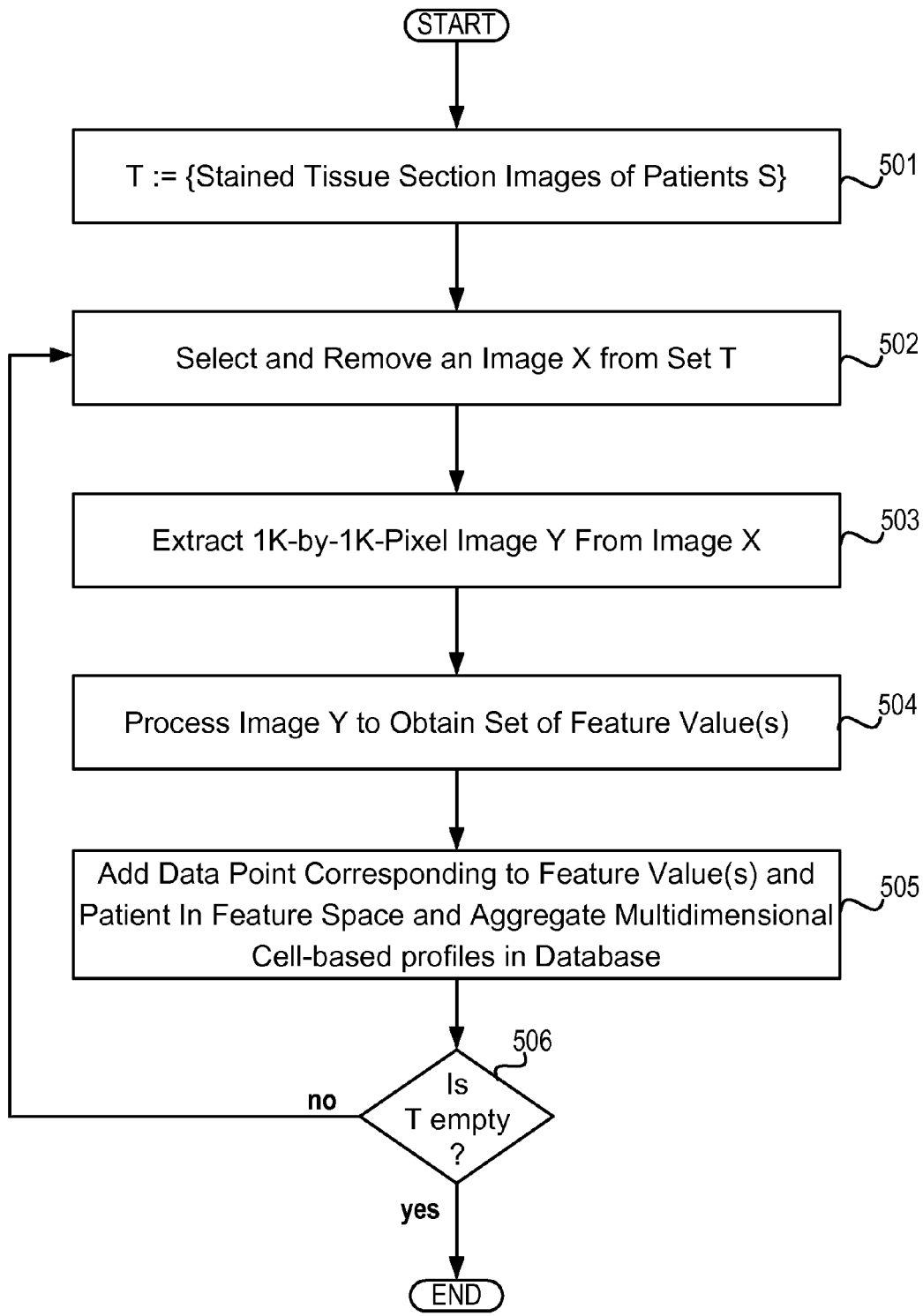
FIG. 5 depicts a flow diagram of an embodiment of a method for obtaining feature values for a plurality of images and plotting the feature values in a feature space.

FIG. 5 depicts a flow diagram of an embodiment of a method for obtaining feature values for a plurality of images and plotting the feature values in a feature space. The method is performed by processing logic that may comprise hardware (circuitry, dedicated logic, etc.), software (such as is run on a general purpose computer system or a dedicated machine), or a combination of both. In one embodiment, the method may be performed by server machine 115 of FIG. 1, and more particularly, by histology image manager 125, while in some other embodiments, one or more blocks of FIG. 5 may be performed by some other machine.

At block 501, a set T is initialized to contain stained tissue section images for the patients of set S. In one implementation, set T contains one stained tissue section image per patient; it should be noted, however, that in some other implementations, there may be a plurality of stained tissues section images for a given patient (or for a plurality of patients), and it will be clear to those skilled in the art, after reading this disclosure, how to adapt the method of FIG. 5 for such implementations.

At block 502, an image X is selected from set T and removed from the set. At block 503, a 1K-by-1K-pixel image Y is extracted from image X. In one implementation, the extraction of image Y from image X is performed by image extractor 201. It should be noted that in some other implementations, an image size other than 1K-by-1K pixels may be used (e.g., 500-by-500 pixels, 2K-by-2K pixels, etc.). Further, it should be noted that in some other implementations, a plurality of images may be extracted from image X, rather than a single image Y, and it will be clear to those skilled in the art, after reading this disclosure, how to adapt the method of FIG. 5 for such implementations.

At block 504, image Y is processed to obtain a set of one or more feature values. An implementation of a method for performing block 504 is described in detail below with respect to FIG. 8.

At block 505, a data point (e.g., a profile associated with a nucleus, etc.) corresponding to the feature value(s) obtained at block 504 and the associated patient are added in a corresponding feature space, and multidimensional cell-based profiles (e.g., features) are aggregated in the database. In one implementation, a data point is added to a single feature space (e.g., a linear feature space for a set having a single feature value, a two-dimensional feature space for a set having a pair of features, etc.). It should be noted that in some other embodiments, a data point may be added at block 505 to a plurality of feature spaces (e.g., added to a first feature space corresponding to two feature values in the set and added to a second feature space corresponding to a third feature value in the set, etc.), and it will be clear to those skilled in the art, after reading this disclosure, how to adapt the method of FIG. 5 for such implementations.

Block 506 branches based on whether set T is empty; if not, execution continues back at block 502, otherwise execution of the method terminates.

Figure 6:
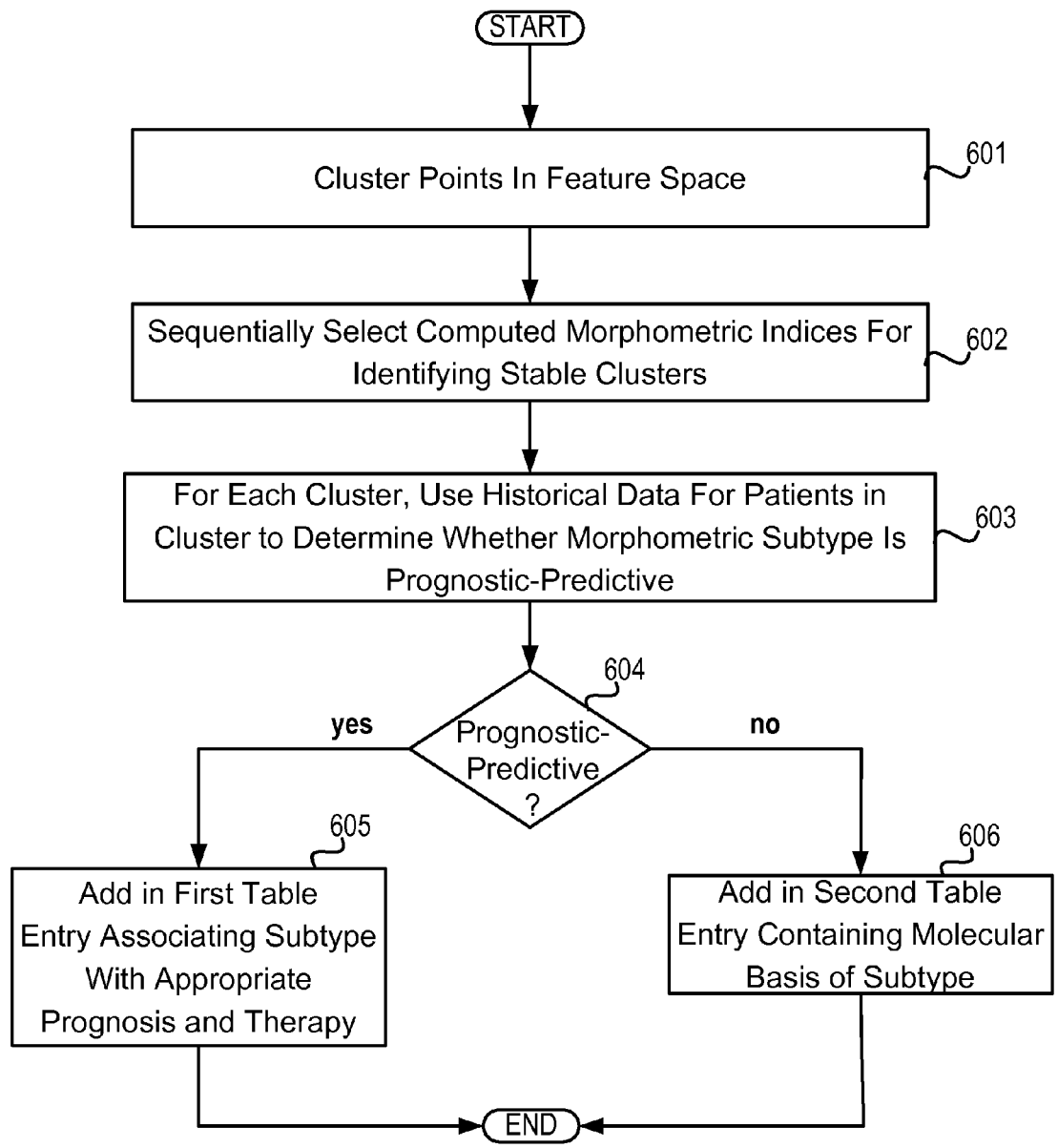
FIG. 6 depicts a flow diagram of an embodiment of a method for obtaining morphometric subtypes and storing associated information in a database.

FIG. 6 depicts a flow diagram of an embodiment of a method for obtaining morphometric subtypes and storing associated information in a database. The method is performed by processing logic that may comprise hardware (circuitry, dedicated logic, etc.), software (such as is run on a general purpose computer system or a dedicated machine), or a combination of both. In one embodiment, the method may be performed by server machine 115 of FIG. 1, and more particularly, by histology image manager 125, while in some other embodiments, one or more blocks of FIG. 6 may be performed by some other machine.

At block 601, points in the feature space are clustered. One particular technique for clustering points is described in detail in Ju Han, Hang Chang, Orsi Giricz, Genee Y. Lee, Frederick L. Baehner, Joe W. Gray, Mina J. Bissell, Paraic A. Kenny, Bahram Parvin: *Molecular Predictors of 3D Morphogenesis by Breast Cancer Cell Lines in 3D Culture. PLoS Computational Biology* 6(2) (2010), which is incorporated by reference in its entirety.

At block 602, subsets of computed morphometric indices are sequentially selected for identifying stable clusters. At block 603, for each cluster, historical data for patients in the cluster (e.g., survival data, etc.) is used to determine whether the morphometric subtype associated with cluster C is prognostic-predictive. In one embodiment, the historical data is stored in prognosis and therapy database 160.

Block 604 branches based on whether the morphometric subtype is determined at block 605 to be prognostic-predictive; if so, execution proceeds to block 605, otherwise execution continues at block 606.

At block 605, an entry associating the morphometric subtype with an appropriate prognosis and therapy (e.g., as determined from the historical data for patients in the corresponding cluster, etc.) is added to a first table of prognosis and therapy database 160. In one embodiment, the first database table corresponds to a table of prognosis and therapy database 160 that associates prognostic-predictive morphometric subtypes with prognoses and therapies (i.e., the first database table corresponds to outcome-based significance (e.g., prognostic, predictive) of computed features). It should be noted that in implementations where prognosis and therapy database 160 is not a relational database (e.g., an object-oriented database, a hierarchical database, etc.), the entry may be added to a data structure other than a table.

At block 606, an entry containing molecular basis of the morphometric subtype is added to a second table of prognosis and therapy database 160. As at block 605, when prognosis and therapy database 160 is not a relational database, the entry may be added to a data structure other than a table. In one embodiment, the second database table corresponds to the table of prognosis and therapy database 160 that stores non-predictive subtypes, while in another embodiment, the second table stores molecular correlates of each subtype per computed subtype/clusters, as described in FIG. 16 of *IEEE Trans Med Imaging*. 2013 *April;* 32(4):670-82. *doi:* 10.1109/ TMI.2012.2231420. *Epub* 2012 *Dec.* 4. *Invariant delineation of nuclear architecture in glioblastoma multiforme for clinical and molecular association*. Chang H, Han J, Borowsky A, Loss L, Gray J W, Spellman P T, Parvin B., which is incorporated by reference in its entirety.

Figure 7:
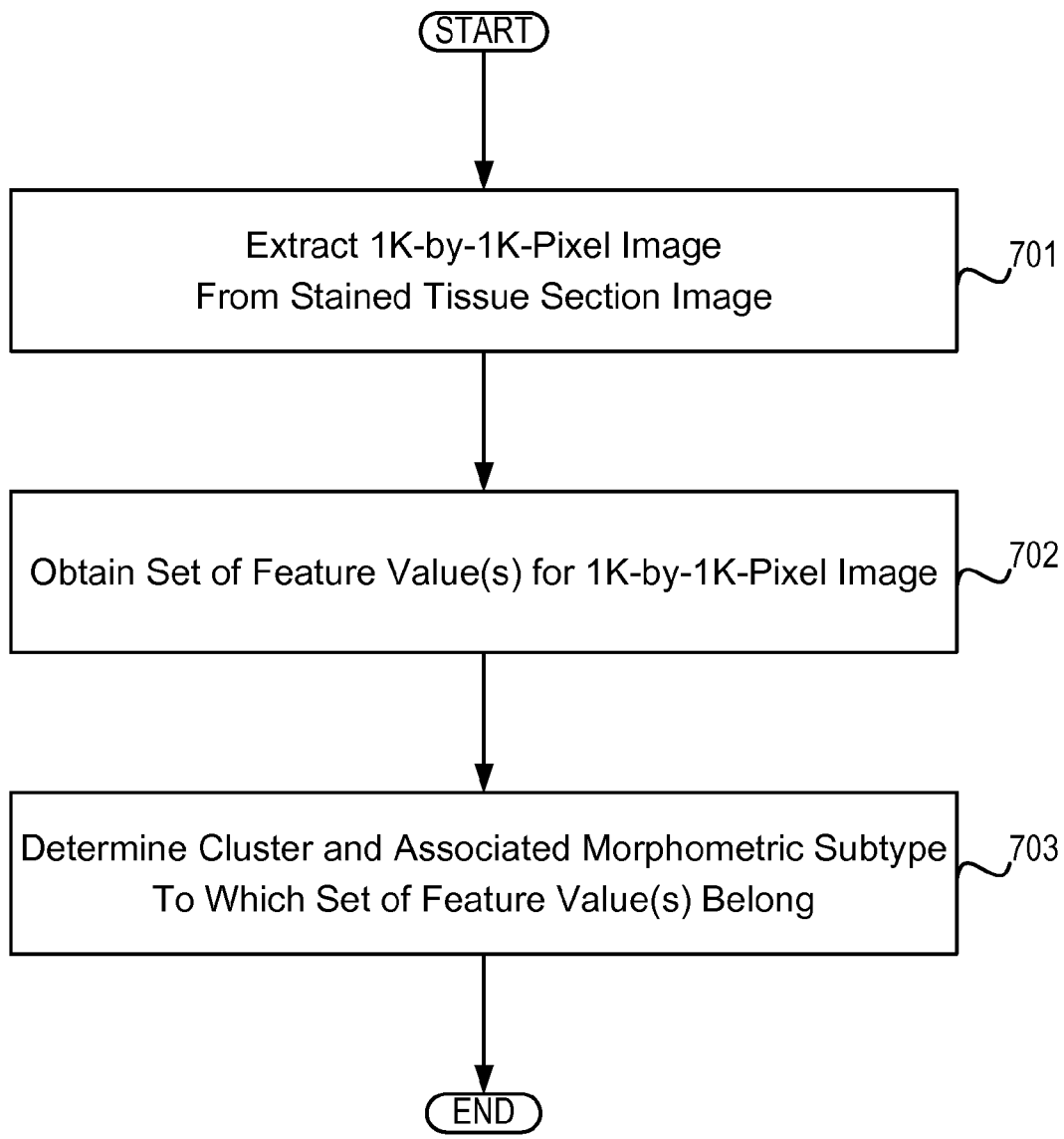
FIG. 7 depicts a flow diagram of an embodiment of a method for determining a morphometric subtype from an image.

FIG. 7 depicts a flow diagram of an embodiment of a method for determining a morphometric subtype from an image. The method is performed by processing logic that may comprise hardware (circuitry, dedicated logic, etc.), software (such as is run on a general purpose computer system or a dedicated machine), or a combination of both. In one embodiment, the method may be performed by server machine 115 of FIG. 1, and more particularly, by histology image manager 125, while in some other embodiments, one or more blocks of FIG. 6 may be performed by some other machine.

At block 701, a 1K-by-1K-pixel image is extracted from an image of a stained tissue section. In one implementation, the extraction is performed by image extractor 201. It should be noted that in some other implementations, an image size other than 1K-by-1K pixels may be used (e.g., 500-by-500 pixels, 2K-by-2K pixels, etc.), while in yet other implementations, block 701 may be omitted and the entire tissue section image processed, rather than a subimage extracted from the image. Further, it should be noted that in some other implementations, a plurality of images may be extracted from the image of the stained tissue section, rather than a single image, and it will be clear to those skilled in the art, after reading this disclosure, how to adapt the method of FIG. 7 for such implementations.

At block 702, a set of one or more feature values is obtained for the 1K-by-1K-pixel image. An implementation of a method for performing block 702 is described in detail below with respect to FIG. 8.

At block 703, the cluster and associated morphometric subtype to which the set of feature value(s) belong is determined. In some implementations, the cluster may be determined by a human (e.g., via visual inspection of a pictorial representation of the feature space, etc.), while in some other implementations, the cluster may be determined mathematically by a machine (e.g., server machine 115, etc.) from the feature values and cluster boundaries.

Figure 8:
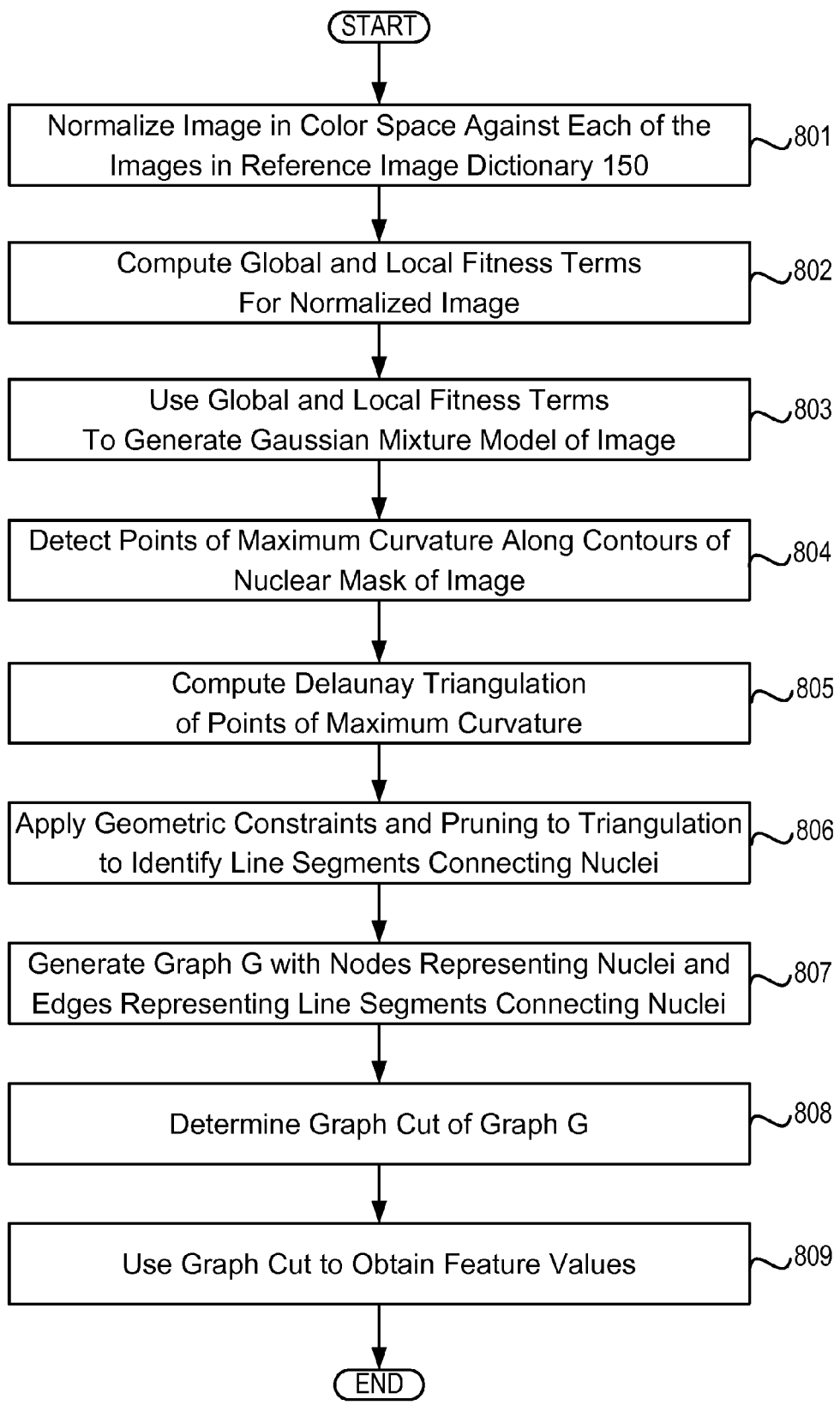
FIG. 8 depicts a flow diagram of an embodiment of a method for obtaining feature values from an image.

FIG. 8 depicts a flow diagram of an embodiment of a method for obtaining feature values from an image. The method is performed by processing logic that may comprise hardware (circuitry, dedicated logic, etc.), software (such as is run on a general purpose computer system or a dedicated machine), or a combination of both. In one embodiment, the method may be performed by server machine 115 of FIG. 1, and more particularly, by histology image manager 125, while in some other embodiments, one or more blocks of FIG. 6 may be performed by some other machine.

At block 801, the image is normalized against each of the images in reference image dictionary 150 in a color space (e.g., red-green-blue [RGB] space, Laplacian of Gaussian [LoG] space, etc.). In one embodiment, the image normalization comprises obtaining an LoG-space representation of the image from a blue ratio representation, where the blue ratio of a pixel (x, y) is computed by the equation:

$$BR(x, y) = \frac{100 \cdot B(x, y)}{1 + R(x, y) + G(x, y)} \cdot \frac{256}{1 + B(x, y) + R(x, y) + G(x, y)}$$

where BR(x, y) is the blue ratio for a pixel (x, y), and R(x, y), G(x, y) and B(x, y) are the red, green and blue intensities, respectively, for pixel (x, y). In one implementation, block 801 is performed by image normalizer 202.

At block 802, global and local fitness terms for the normalized image are computed. In one implementation, the global and local fitness terms are computed in accordance with the equations:

$$E_{gf}(x_p = i) = -\sum_{k=1}^{N} \lambda^k \log(p_i^k(f^k(p))) - \alpha \cdot \sum_{k=N+1}^{N} \lambda^{k-N} \log(p_i^k(f^k(p)))$$

and $$E_{lf}(x_p=i)=-\gamma \log(p_i(f(p)))$$

where $E_{gf}(x_p=i)$ is the global fitness term that represents proximity of a pixel in a test image to those in the reference images. The $\lambda$ parameter is computed automatically by associating a test image against reference images, as per *IEEE Trans Med Imaging*. 2013 *April;* 32(4):670-82. *doi:* 10.1109/ TMI.2012.2231420. *Epub* 2012 *Dec.* 4. *Invariant delineation of nuclear architecture in glioblastoma multiforme for clinical and molecular association*. Chang H, Han J, Borowsky A, Loss L, Gray J W, Spellman P T, Parvin B.

At block 803, a Gaussian Mixture Model of the image is generated using the global and local fitness terms computed at block 802. One particular technique for generating the Gaussian Mixture Model is described in detail in *IEEE Trans Med Imaging*. 2013 *April;* 32(4):670-82. *doi:* 10.1109/ TMI.2012.2231420. *Epub* 2012 *Dec.* 4. *Invariant delineation of nuclear architecture in glioblastoma multiforme for clinical and molecular association*. Chang H, Han J, Borowsky A, Loss L, Gray J W, Spellman P T, Parvin B., which is incorporated by reference in its entirety. In one implementation, block 803 is performed by image modeler 203.

At block 804, points of maximum curvature are detected along contours of a nuclear mask of the image, and at block 805, a Delaunay triangulation of the points of maximum curvature is computed. Particular techniques for performing block 804 and 805 are described in detail in Quan Wen, Hang Chang, Bahram Parvin: *A Delaunay Triangulation Approach for Segmenting Clumps of Nuclei. ISBI* 2009: 9-12, which is incorporated by reference in its entirety. In one implementation, blocks 804 and 805 are performed by graph and geometric engine 204.

At block 806, geometric constraints and pruning are applied to the Delaunay triangulation to identify line segments connecting nuclei in the image. Particular techniques for performing block 806 are described in detail in Quan Wen, Hang Chang, Bahram Parvin: *A Delaunay Triangulation Approach for Segmenting Clumps of Nuclei. ISBI* 2009: 9-12, which is incorporated by reference in its entirety. In one implementation, block 806 is performed by graph and geometric engine 204.

At block 807, a graph G is generated, where the nodes of G correspond to the nuclei of the image and the edges of G correspond to the line segments identified at block 806, and at block 808, a cut of graph G is determined. Particular techniques for performing these operations are described in detail in Quan Wen, Hang Chang, Bahram Parvin: *A Delaunay*

*Triangulation Approach for Segmenting Clumps of Nuclei. ISBI* 2009: 9-12, which is incorporated by reference in its entirety. In one implementation, blocks 806 and 807 are performed by graph and geometric engine 204.

At block 809, the cut of graph G is used to obtain values of features of the image (e.g., average nuclear size, maximum nuclear size, minimum nuclear size, variance in nuclear size, cellularity, etc.). One particular technique for extracting feature values is described in detail in Ju Han, Hang Chang, Kumari L. Andarawewa, Paul Yaswen, Mary Helen Barcellos-Hoff, Bahram Parvin: *Multidimensional Profiling of Cell Surface Proteins and Nuclear Markers. IEEE/ACM Trans. Comput. Biology Bioinform.* 7(1): 80-90 (2010), which is incorporated by reference in its entirety.

Figure 9:
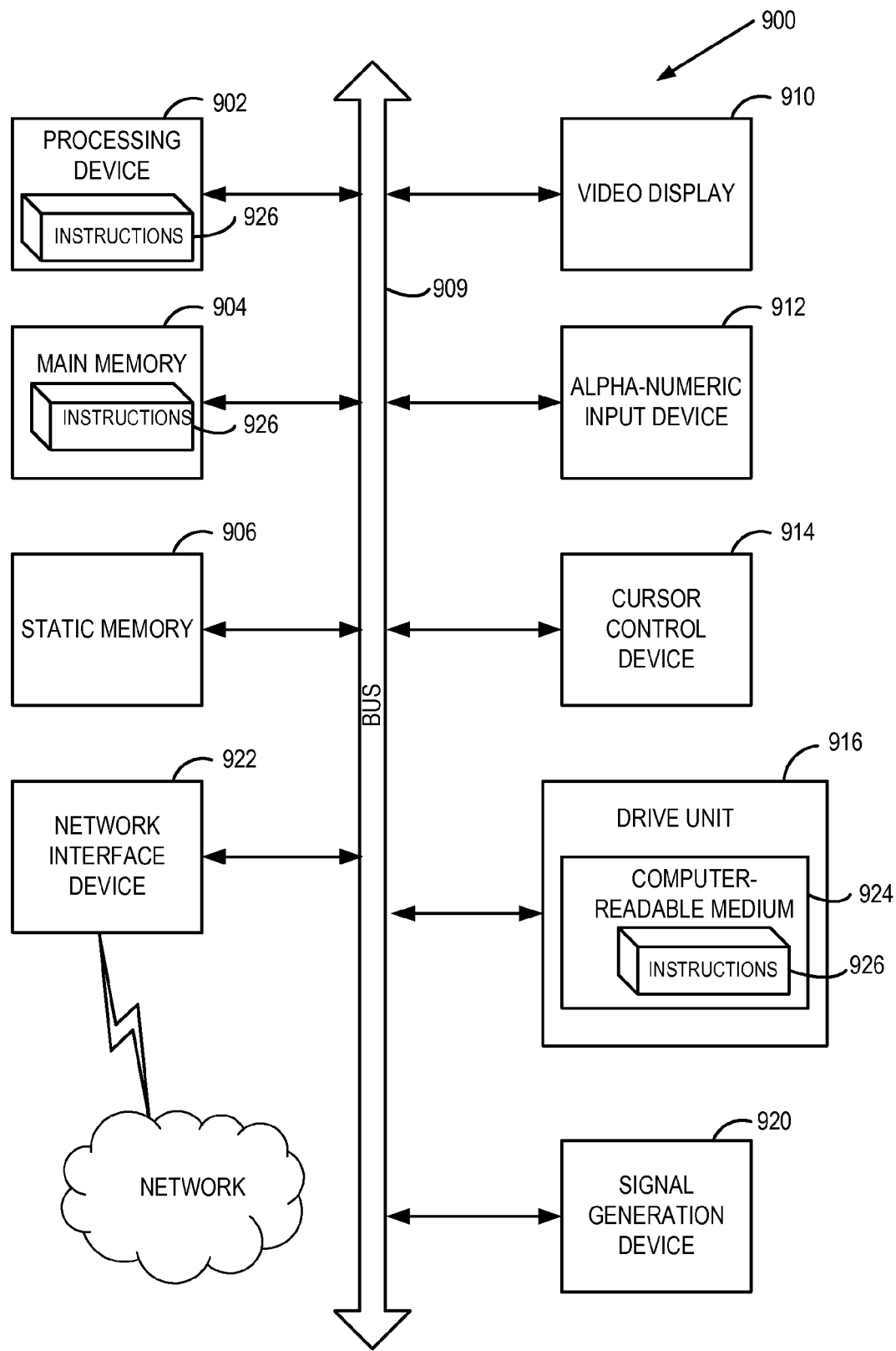
FIG. 9 depicts a block diagram of an illustrative computer system operating in accordance with aspects and implementations of the present disclosure.

FIG. 9 illustrates an exemplary computer system within which a set of instructions, for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server machine in client-server network environment. The machine may be a personal computer (PC), a server, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 900 includes a processing device 902, a main memory 904 (e.g., read-only memory (ROM), flash memory, dynamic random access memory (DRAM) such as synchronous DRAM (SDRAM)), a static memory 906 (e.g., flash memory, static random access memory (SRAM)), and a data storage device 916, which communicate with each other via a bus 909.

Processing device 902 represents one or more general-purpose processing devices such as a microprocessor, central processing unit, or the like. More particularly, the processing device 902 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 902 may also be one or more special-purpose processing devices such as an application specific integrated circuit (ASIC), a field programmable gate array (FPGA), a digital signal processor (DSP), network processor, or the like. The processing device 902 is configured to execute instructions 926 for performing the operations and steps discussed herein (e.g., instructions for executing blocks of the methods of FIGS. 3 through 8, etc.).

The computer system 900 may further include a network interface device 922. The computer system 900 also may include a video display unit 910 (e.g., a liquid crystal display (LCD) or a cathode ray tube (CRT)), an alphanumeric input device 912 (e.g., a keyboard), a cursor control device 914 (e.g., a mouse), and a signal generation device 920 (e.g., a speaker).

The data storage device 916 may include a computer-readable medium 924 on which is stored one or more sets of instructions 926 (e.g., instructions executed by histology image manager 125, etc.) embodying any one or more of the methodologies or functions described herein. Instructions 926 may also reside, completely or at least partially, within the main memory 904 and/or within the processing device 902 during execution thereof by the computer system 900, the main memory 904 and the processing device 902 also constituting computer-readable media. Instructions 926 may further be transmitted or received over a network via the network interface device 922.

While the computer-readable storage medium 924 is shown in an exemplary embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the above description, numerous details are set forth. It will be apparent, however, to one of ordinary skill in the art having the benefit of this disclosure, that embodiments may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "receiving," "extracting," "processing," "associating," "determining," "detecting," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Aspects and implementations of the disclosure also relate to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present disclosure is not described with reference to any particular programming language. It will be appreciated that a variety of programming languages may be used to implement the teachings of the disclosure as described herein.

We have recently completed the first large scale analysis of the whole mount tissue sections from multiple tumor types of approximately 1000 sections, and posted the segmentation and computed morphometric indices on our Web site. We are currently using this data for hypothesis generation through subtyping and molecular association, as are many other institutes. Our current operational pipeline downloads images and clinical information, partitions each tissue section (in the order of 40,000-by-40,000 pixels or higher at 20×) into blocks of 1000-by-1000 pixels, submits the blocks to a system (currently one of the clusters at the National Energy Research Scientific Computing Center (NERSC at Berkeley Lab)), and imports computed representation back to an in-house developed database. All computed representation and visualization of large scale tissue sections are accessible through TCGA's web site. One particular utility is to allow users to overlay computed representation (e.g., segmentation results) on a large scale tissue section and view them like an interactive online map for quality control and interactions with the onboard clinicians and pathologists.

From an image-based modeling perspective, the novelties aim at removing the batch effect and representing tumor architecture at the cellular (e.g., single cell analysis) and region levels (e.g., small patches with approximately 20-50 cells). At the cellular level, the main challenges are technical variations and biological heterogeneity. Technical variations originate from the fact that histology sections from paraffin-embedded blocks are produced at different laboratories (or the same laboratory on different dates), and are subject to deviations in (i) fixation and staining protocols, (ii) inconsistencies of scanning resolution, and (iii) the presence of anomalies (e.g. folds, stretches) that may introduce artifacts in data processing. The first artifact is referred as the batch effect and resolved computationally. The second artifact is resolved by reading the header information from the SVS file, and to process images at a constant resolution. The third artifact is curated manually. Biological heterogeneity originates from variations in cell type, nuclear size, chromatin intensity, cellular organization, and cytoplasmic signature. Therefore, computational methods need to be invariant to scale and intensity. For example, methods that rely on nuclear seed detection will be error-prone because of wide variation of nuclear size. At some level, the batch effect and tumor heterogeneity can be coupled. For example, a close examination of the GBM dataset indicates that the eosin stain (the pink region) is also non-uniform within a small region (e.g., sub-colony) of a tissue section, which can be a consequence of secretion of macromolecules as a result of cellular stress. Our solution is to address the batch effect and tumor heterogeneity together by modeling foreground and background with an annotated reference library. To our knowledge, supported by publications and preliminary results, we have developed and implemented the most robust system for removing the batch effect for the task of nuclear segmentation. At the regional level, the main challenge is a representation that best captures underlying tumor signatures based on color and texture. Here, we introduce the concept of automatic learning of invariant kernels, as opposed to manually designed feature detectors, for capturing intrinsic properties of spatial distributions. At both levels of cellular and patch-level representations, the challenge will be a well curated dataset that best captures diversity and heterogeneity.

The present examples and methods are intended to empower pathologists and clinicians with new technologies that can only be rendered with a large cohort that TCGA can offer. From a computational perspective, we offer innovative new algorithms to represent tumor sections at cellular and regional (e.g., patch) levels. Once such a representation is computed (e.g., in the form of a large data matrix), the basic knowledge for genomic and clinical association already exists to query and interrogate different views of the data with respect to an outcome. The end result is a knowledge repository where molecular bases of prognostic morphometric subtypes and tumor heterogeneity can be detected, analyzed and utilized for diagnostic and prognostic purposes.

In two related experiments, we examined the prognostic and predictive powers of (I) computed morphometric indices and (II) a heterogeneity index for a cohort of 146 Glioblastoma Multiforme (GBM) patients. In (I), we observed that many morphometric indices were highly informative. For example, the intensity of the cytoplasmic staining was both prognostic and predictive following cross validation. Our analysis indicated two subtypes for cytoplasmic features, where basophilic cytoplasm results in a worse prognosis, but responds better to the more aggressive therapy. A potential biological interpretation points to the failure of the eosinphilic cells to arrest growth in order to repair chemotherapy-inflicted damage. In (II), we partitioned each whole mount tissue section in a cohort, into 1 k-by-1 k blocks, where subtyping was limited to the amount of information within the block. Based on the cellularity index, such an approach revealed 4 subtypes. Subsequently, a whole mount tissue section was represented in terms of the intrinsic computed subtypes of the entire cohort for quantifying heterogeneity per tissue section. We then divided patients into 4 subpopulations based on cellularity and heterogeneity indices. The subpopulation of low heterogeneity and high cellularity were better predictive of a more aggressive therapy. This result was cross validated.

We have initiated two collaborative efforts with UCSF (brain and breast cancer spores) that are part of a clinical trial with well curated pathology and clinical reports. The brain SPORE has collected 2 biopsies per patient to form a cohort of 400 patients with ex-vivo measurements and metrics derived from magnetic resonance imaging (MRI). The study enables discovery of non-invasive biomarkers and predicting outcomes (e.g., survival, resistance to chemotherapy, recurrence) based on computed morphometric data. (iii) A unique aspect of our morphometric analysis pipeline is the role of heterogeneity in predicting the outcome. This type of annotation is absent in all pathology reports, and, based on our preliminary results and the current trend in cancer research, there is a need to validate heterogeneity for potential inclusion in the CAP report. In all 3 levels, we will compare computed morphometric indices with and without the CAP report, and the CAP report by itself to evaluate prognostic and predictive power. All multivariate analysis will be based on the Cox proportional hazard model.

Curation of prognostic and predictive morphometric subtypes: The current computational pipeline generates approximately 52 indices per cell that represents morphometric and organization attributes. Patch-level analysis will also provide gross compositional representation that is of value for some tumor types. We have recently demonstrated the value of subtyping at the patient-level and at block-level for the entire cohort. At a macro scale, we will construct and curate a repository of patient level prognostic subtypes based on (i) a single morphometric index, (ii) pairwise indices, (iii) those in the transformed spaces (e.g., dimensionality reduction of either PCA, MDS or isomap), and (iv) entropy ranking for preserving the meaningfulness of computed indices. At a micro level, we will explore policies to represent heterogeneity. Our current policy is to divide each whole mount tissue section in a cohort, into 1 k by-1 k blocks, where subtyping will be limited to the amount of information within the block. Computed indices for tumor heterogeneity will utilize the Cox proportional hazard model to explore the relationship between the survival distribution and compositional covariates subject to clinical covariates.

Molecular basis of heterogeneity: In a recent experiment, we performed correlative analysis between computed heterogeneity index from histology sections and transcriptome data for the GBM cohort. A subset of the transcripts was then selected with FDR of less than 0.15. VEGF-A, CD36, and LOX (among others) are shown to be highly correlative with the computed heterogeneity index. Most of these transcripts are known to be associated with different facets of cancer development and confirmed by TCGA's gene ranker site; however, their association with tumor heterogeneity has not been previously reported. For example, VEGF-A, the primary pro-angiogenic factor in GBM is upregulated as tumors become more heterogeneous, with concomitant downregulation of CD36. Conversely, VEGF-A becomes down-regulated as tumors become highly cellular. CD36 is the receptor for the anti-angiogenic molecule thrombospondin, and it is necessary to enable thrombospondin to block the proangiogenic activities of VEGF-A, and to induce apoptosis in endothelial cells. Therefore, both the increase in VEGF-A along with the decrease in CD36, seen with increasing heterogeneity, would be pro-angiogenic. A potential rationale can be based on the dynamics of tumor formation in that heterogeneity can recruit microvasculature formation, but is modulated by tumor growth via high cellularity phenotype, i.e., when vasculatures are formed. This rationale concurs with the histology sections of high cellularity regions, emergence of microvasculature, and observing that vasculatures are absent in less cellular regions. Another analogy can be drawn from wound healing, where VEGF-A is upregulated upon sudden disruption of cellularity, which is then followed by recruitment of microvasculature. It has also been shown that endothelial cells create a niche that promotes cancer stem cells in GBM. Conversely, it has also been suggested that tumor progenitor cells can be involved in the endothelial transdifferentiation. This concept of self-renewal, via the stem cell niche of endothelial cells, is also synergistic with metastasis through upregulation of the LOX transcript as well as a function of increased heterogeneity and/or simultaneous reduction in cellularity. This analysis show that computed heterogeneity from histology sections can forward a testable hypothesis for therapeutic intervention (e.g., antiangiogenic therapy for heterogeneous tumors). To remove barriers for hypothesis generation by (i) identifying association between morphometric indices and genome-wide molecular data, (ii) predicting molecular basis of computed subtype and heterogeneity indices, and (iii) utilizing sparse regression for multivariate analysis.

We will develop a pipeline to identify the molecular basis of (ii) each prognostic morphometric subtype, and (ii) heterogeneity indices. Both univariate and multivariate associations (see next section) will be utilized to infer molecular subsets of each subtype as before. Similarly, the molecular basis of tumor heterogeneity will also be inferred through regression analysis. The pipeline will be designed to pre-compute and update the molecular basis of subtypes and heterogeneity as new data becomes available. Thus creating a knowledge base, where computed representations can be queried on demand, and accessed through a REST-like API. Furthermore, web pages will be built to provide different views of computed representations. In designing the interfaces, we will also adopt the model that has been employed by cBio Cancer Portal for its transparent functionality.

It is to be understood that the above description is intended to be illustrative, and not restrictive. Many other embodiments will be apparent to those of skill in the art upon reading and understanding the above description. Moreover, the techniques described above could be applied to other types of data instead of, or in addition to, media clips (e.g., images, audio clips, textual documents, web pages, etc.). The scope of the disclosure should, therefore, be determined with reference to the appended claims, along with the full scope of equivalents to which such claims are entitled.

What is claimed is:

1. A method comprising:
processing, by a processing device, an image of a stained tissue section of a patient;
extracting from the processed image a set of feature values for a set of cell-based features;
associating, based on the set of feature values, the processed image with a particular cluster of a plurality of clusters, wherein the plurality of clusters is defined with respect to a feature space corresponding to the set of features, wherein the particular cluster identifies a morphometric subtype; and
determining whether the morphometric subtype is prognostic-predictive and, in response:
characterizing heterogeneity of a tumor of the patient and evaluating whether heterogeneity is more virulent in terms of prognosis or prediction, and
inferring molecular correlates of a compute morphometric subtype through association with genome-wide molecular data for the tumor.

2. The method of claim 1 wherein the processing of the image comprises normalizing the image in a color map space with respect to a plurality of reference images, and wherein the method further comprises determining at least one of a prognosis or a therapy for the patient based on the particular cluster and historical data associated with the particular cluster.

3. The method of claim 2 wherein the reference images are represented in the feature space as a Gaussian Mixture Model.

4. The method of claim 1 wherein the processing of the image comprises using an image-based model to remove technical variation and biological heterogeneity.

5. The method of claim 1 wherein the processing of the image comprises applying a graph cut to the subimage to identify nuclei.

6. The method of claim 1 further comprising administering the therapy.

7. The method of claim 1 wherein the processing of the image comprises applying one or more geometric constraints to infer edges between nuclei.

8. A non-transitory computer readable storage medium including instructions that, when executed by a processing device, cause the processing device to perform operations comprising:
 determining, by the processing device and based on historical data, whether a morphometric subtype of a set of histology sections is prognostic-predictive; and
 in response to determining that the morphometric subtype is prognostic-predictive:
  determining, by the processing device and based on the historical data, at least one of a prognosis or a therapy for the morphometric subtype, and
  populating, by the processing device, a database with a record that associates the morphometric subtype with the at least one of the prognosis or the therapy.

9. The non-transitory computer readable storage medium of claim 8 wherein the morphometric subtype is determined via clustering of a plurality of feature sets in a feature space, and wherein each of the plurality of feature sets is obtained by processing an image of a respective set of histology sections.

10. The non-transitory computer readable storage medium of claim 9 wherein the processing of the image comprises normalizing the image in a color map space with respect to a plurality of reference images.

11. The non-transitory computer readable storage medium of claim 9 wherein the processing of the image comprises representing the image in the feature space as a Gaussian Mixture Model.

12. The non-transitory computer readable storage medium of claim 9, further comprising in response to determining that the morphometric subtype is prognostic-predictive:
 characterizing tumor heterogeneity and evaluating whether heterogeneity is more virulent in terms of prognosis or prediction, and
 inferring molecular correlates of a compute morphometric subtype through association with genome-wide molecular data for a tumor.

13. The non-transitory computer readable storage medium of claim 9 wherein the processing of the image comprises applying a graph cut to the subimage to identify nuclei.

14. The non-transitory computer readable storage medium of claim 9 wherein the processing of the image comprises detecting points of maximum curvature along a contour of a nuclear mask and triangulating the points of maximum curvature.

15. The non-transitory computer readable storage medium of claim 9 wherein the processing of the image comprises applying one or more geometric constraints to infer edges between nuclei.

16. A system comprising:
 a memory to store an image of a stained tissue section of a patient; and
 a processing device operatively coupled with the memory, the processing device to:
  process the image,
  extract from the processed image a set of feature values for a set of cell-based features,
  associate, based on the set of feature values, the processed image with a particular cluster of a plurality of clusters, wherein the plurality of clusters is defined with respect to a feature space corresponding to the set of features, and
  determine a quantification of a tumor property that identifies an intrinsic subtype.

17. The system of claim 16 wherein to process the subimage, the processing device is to normalize the subimage in a color map space with respect to a plurality of reference images.

18. The system of claim 16 wherein the set of cell-based features comprises average nucleus size.

19. The system of claim 16 wherein to process the subimage, the processing device is to apply at least one of a local fitness term or a global fitness term.

20. The system of claim 16 wherein to process the subimage, the processing device is to apply a graph cut to the subimage to identify nuclei.

* * * * *